(12) United States Patent
Cohen et al.

(10) Patent No.: US 8,221,370 B2
(45) Date of Patent: Jul. 17, 2012

(54) PERSONAL CARE ARTICLE WITH SUBSTRATE SURFACE TOPOGRAPHY FOR EVOKING A NEUROSENSORY SKIN RESPONSE

(75) Inventors: Jason C. Cohen, Appleton, WI (US); David W. Koenig, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 520 days.

(21) Appl. No.: 11/931,419

(22) Filed: Oct. 31, 2007

(65) Prior Publication Data
US 2009/0118690 A1    May 7, 2009

(51) Int. Cl.
*A61F 13/15* (2006.01)
*A61F 13/20* (2006.01)

(52) U.S. Cl. .................... 604/385.01; 604/367; 604/382
(58) Field of Classification Search .................. 604/365, 604/378–380, 382–384, 385.01, 385.06, 604/385.101
See application file for complete search history.

(56) References Cited

U.S. PATENT DOCUMENTS

| | | | |
|---|---|---|---|
| 3,072,914 A | 1/1963 | Velonis et al. | |
| 3,148,235 A | 9/1964 | Velonis et al. | |
| 3,761,965 A | 10/1973 | Barasch | |
| 4,084,265 A | 4/1978 | Anfelt | |
| 4,745,635 A | 5/1988 | Kinnear | |
| 5,448,777 A | 9/1995 | Lew | |
| 5,467,481 A | 11/1995 | Srivastava | |
| 5,794,266 A | 8/1998 | Han | |
| 5,817,400 A * | 10/1998 | Chen et al. | 428/153 |
| 5,958,976 A | 9/1999 | Muizzuddin et al. | |
| 5,983,395 A | 11/1999 | Lei | |
| 6,048,600 A | 4/2000 | Hansson | |
| 6,322,665 B1 | 11/2001 | Sun et al. | |
| 6,326,901 B1 * | 12/2001 | Gonzales | 340/7.2 |
| 6,362,391 B1 | 3/2002 | Mizutani et al. | |
| 6,455,592 B1 | 9/2002 | Laugier et al. | |
| 6,562,794 B1 | 5/2003 | Lanzendorfer et al. | |

(Continued)

FOREIGN PATENT DOCUMENTS

EP   0 919 212 A2 *  6/1999
KR   1019980081143 A   11/1998

(Continued)

OTHER PUBLICATIONS

Gescheider, Some Characteristics of Tactile Channels, May 6, 2003, Elsevier, Behavioural Brain Research 148 (2004), p. 35-40.*

(Continued)

*Primary Examiner* — Michele M Kidwell
(74) *Attorney, Agent, or Firm* — Armstrong Teasdale LLP

(57) ABSTRACT

In a personal care article for contact with human skin, a non-woven substrate of the article has a longitudinal direction, a transverse direction and at least one skin-contact surface. A plurality of surface features is disposed on the at least one skin-contact surface in a sinusoidal wave-form along at least one of the longitudinal direction and the transverse direction of the substrate. The surface features have a height that generally defines an amplitude of the sinusoidal waveform, and are spaced from each other a spatial distance. This spatial distance is at least in part a function of a movement speed at which the article is to be moved relative to the skin while in contact therewith. In one method of making such a substrate, the movement speed and a temporal frequency are selected and used to determine the spacing between surface features on the skin-contact surface of the substrate.

11 Claims, 2 Drawing Sheets

U.S. PATENT DOCUMENTS

| | | | |
|---|---|---|---|
| 6,858,000 | B1 | 2/2005 | Schukin et al. |
| 6,879,848 | B2 | 4/2005 | Lygas |
| 2005/0059664 | A1 | 3/2005 | Gil et al. |
| 2005/0288647 | A1 | 12/2005 | Ellingson et al. |
| 2006/0218697 | A1 | 10/2006 | Modha et al. |
| 2007/0136926 | A1 | 6/2007 | Johnson et al. |

FOREIGN PATENT DOCUMENTS

| | | |
|---|---|---|
| WO | 0220056 A2 | 3/2002 |
| WO | 03091281 A1 | 11/2003 |
| WO | 03093479 A1 | 11/2003 |

OTHER PUBLICATIONS

Gescheider, G. A., et al, The Effects of Aging on Information-Processing Channels in the Sense of Touch: I. Absolute Sensitivity, Somatosensory and Motor Research, Oct. 18, 1994, pp. 345-357, vol. 11, No. 4.

Johnson, Kenneth, O., et al, Neural Mechanisms of Spatial Tactile Discrimination: Neural Patterns Evoked by Braille-Like Dot Patterns in the Monkey, Journal of Physiology, 1981, pp. 117-144, The Physiological Society.

Bolanowski, Jr., et al., Four Channels Mediate the Mechanical Aspects of Touch, Journal of Acoustical Society of America, Nov. 1988, pp. 1680-1694, Issue 84 (5), Acoustical Society of America, USA.

Militky, Jiri, et al., Surface Roughness and Fractal Dimension, Date Unknown, 23 pages.

International Search report for PCT/IB2008/053939, dated Jun. 24, 2009, 4 pages.

\* cited by examiner

PERSONAL CARE ARTICLE WITH SUBSTRATE SURFACE TOPOGRAPHY FOR EVOKING A NEUROSENSORY SKIN RESPONSE

BACKGROUND

This invention relates generally to personal care products that include a non-woven substrate, more particularly such a non-woven substrate that is intended for contact with human skin while the substrate is moved relative to the subject's skin, as in the manner of a tissue or wet wipe, and even more particularly to such a non-woven substrate that is configured to evoke a desired neurosensory skin response when moved relative to the subject's skin while in contact therewith.

Personal care products that comprise or otherwise incorporate a non-woven substrate come in many different forms including without limitation, for example, dry or wet wipes, absorbent articles such as diapers, training pants, feminine care products and bandages, medical garments, bath tissue and facial tissue. Wet wipes, for example, typically contain a cream, lotion, ointment or other substance that is applied to one's skin by rubbing or wiping the wipe relative to skin while in contact therewith to deliver the substance onto the skin for treatment thereof. Some functional attributes provided by such products are often transparent to the subject person. To this end, these personal care products may also include a perception characteristic such as color, smell, visual texture and/or tactile features to enhance the user's experience and provide the user with a positive indication or perception of the functional attribute of the personal care article. For example, colored dots have been used to signify activity of an anti-viral facial tissue; visual texture in bath tissue is linked to enhanced cleaning; drapability of wipes provides a perception of softness; and fragrances in toiletries may imply freshness.

Of these perception characteristics, tactile features and more particularly features intended to purposefully stimulate the neurosensory skin function have been insufficiently explored. In one known model of mechanoreception, referred to as a four-channel model, four information-processing channels exist for the human skin, with each channel being mediated by a morphologically distinct receptor type innervated by a specific nerve fiber type and tuned to a different range of frequencies. In general, the four psychophysical channels at their absolute thresholds have overlapping frequency characteristics for detection of sinusoidal vibration, with each channel optimally tuned to a specific region of the spectrum.

There is a need, therefore, for a non-woven substrate configured (e.g., having tactile surface features) to target a particular mechanoreceptor response when rubbed against human skin, and more particularly such a configuration that takes into account the expected speed at which the substrate will be rubbed against a particular skin region of a person. For example, such a response may be a positive response allowing for a pleasing feel to the user. Alternatively, the response can be such that the sensory response is lost (i.e., the subject against whose skin the substrate is being rubbed has little or no sense of the rubbing), allowing for treatment of itch or irritation symptoms.

SUMMARY OF THE DISCLOSURE

In one embodiment, a personal care article for contact with human skin upon movement of the article over the skin at a movement speed of the article relative to the skin generally comprises a non-woven substrate having a longitudinal direction, a transverse direction and at least one skin-contact surface. A plurality of surface features is disposed on the at least one skin-contact surface in a sinusoidal wave-form along at least one of the longitudinal direction and the transverse direction of the substrate. The surface features have a height that generally defines an amplitude of the sinusoidal waveform, and are spaced from each other a spatial distance. This spatial distance is at least in part a function of the movement speed at which the article is to be moved relative to the skin while in contact therewith.

In another embodiment, a personal care article for contact with human skin upon movement of the article over the skin at a movement speed of the article relative to the skin generally comprises a non-woven substrate having a longitudinal direction, a transverse direction and at least one skin-contact surface. A plurality of surface features is disposed on the at least one skin-contact surface in a sinusoidal wave-form along at least one of the longitudinal direction and the transverse direction of the substrate. The surface features are sized and located on the skin-contact surface of the non-woven substrate to evoke, upon movement of the article over the skin in contact therewith, a positive stimulatory response of a P-channel skin receptor of a four-channel model of mechanoreception. The response is at a temporal frequency in the range of about 200 Hz to about 400 Hz.

In one embodiment of a method of making a substrate for movement relative to human skin while in contact therewith, a movement speed at which the substrate is to be moved over the human skin with the skin-contact surface in contact with the skin is selected. A temporal frequency at which the skin is to be subjected to the skin-contact surface upon movement of the substrate relative to the skin while in contact therewith is also selected. A spatial distance between surface features on the skin-contact surface is determined based at least in part on the selected movement speed. Surface features are then located on the skin-contact surface of the substrate to define a sinusoidal wave-form topography with the surface features being spaced from each other a distance that is substantially the determined spatial distance between surface features.

In a series of personal care articles for contact with the human skin according to one embodiment, such a series of articles generally comprises a first personal care article for contact with human skin upon movement of the article over the skin at a first movement speed of the article relative to the skin. The first personal care article generally comprises a first non-woven substrate having a longitudinal direction, a transverse direction and at least one skin-contact surface, and a plurality of surface features disposed on the at least one skin-contact surface in a sinusoidal wave-form along at least one of the longitudinal direction and the transverse direction of the first substrate. The surface features have a height that generally defines an amplitude of the sinusoidal wave-form, and are spaced from each other a first spatial distance. This first spatial distance is at least in part a function of the first movement speed at which the first article is to be moved relative to the skin while in contact therewith.

The series further generally comprises a second personal care article for contact with human skin upon movement of the article over the skin at a second movement speed of the article different from the first movement speed at which the first personal care article is moved relative to the skin. The second personal care article generally comprises a second non-woven substrate having a longitudinal direction, a transverse direction and at least one skin-contact surface, and a plurality of surface features disposed on the at least one skin-contact surface in a sinusoidal wave-form along at least one of the longitudinal direction and the transverse direction of the second substrate. The surface features have a height that generally defines an amplitude of the sinusoidal waveform, and are spaced from each other a second spatial distance different from the first spatial distance. The second spatial distance is at least in part a function of the second movement speed at which the second article is to be moved relative to the skin while in contact therewith.

BRIEF DESCRIPTION OF THE DRAWINGS

Corresponding reference characters indicate corresponding parts throughout the drawings.

DETAILED DESCRIPTION

Figure 1:
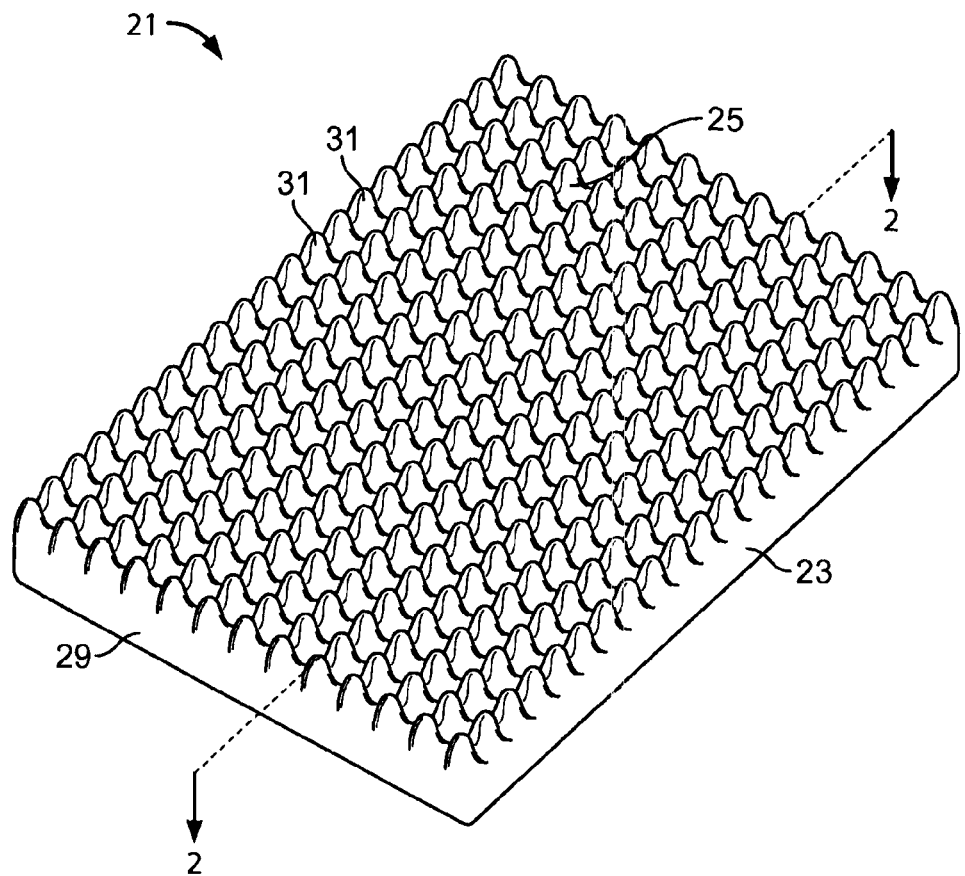
FIG. 1 is a perspective view of one embodiment of a personal care article illustrated in the form of a wet wipe.

With reference now to the drawings and in particular to FIG. 1, one embodiment of a personal care article is illustrated and further described herein in the form of a wipe (indicated generally at 21) such as a dry wipe or a wet wipe intended to be rubbed or wiped against human skin so as to treat the skin or otherwise apply a treating substance or composition to the skin. In the particular illustrated embodiment the personal care article, and in particular the wipe 21, comprises a non-woven substrate 23 which substantially defines the entire article. It is understood, however, that the personal care article may be other than a wipe 21, such as a bath tissue, facial tissue or other article comprised primarily of a non-woven substrate. It is also contemplated that the personal care article may have multiple components and incorporate a non-woven substrate as one component thereof, such as medical garments, bandages, cosmetic articles and absorbent articles including, without limitation, diapers, training pants, adult incontinence garments and feminine care articles, in which the non-woven substrate is intended to contact the wearer's skin.

The non-woven substrate 23 suitably has a skin-contact surface 25, broadly, a first skin-contact surface, intended for contact with human skin (whether the skin is that of the user of the personal care article, or of another person being treated by a caregiver), and a second surface 27 opposite the skin-contact surface (i.e., on an opposite side of the substrate 23). The non-woven substrate 23 suitably comprises a fibrous non-woven web 29 that at least forms the first skin-contact surface of the substrate and may form the entirety of the substrate. As used herein a non-woven web 29 refers to a structure of individual fibers or filaments randomly arranged in a mat-like fashion that may but need not necessarily include a binder material to facilitate binding together of the fibers. Suitable non-woven webs 29 may be made from a variety of known processes including, but not limited to, airlaid processes, wet-laid processes such as with cellulosic-based tissues or towels, coforming processes, hydroentangling processes, staple fiber carding and bonding, and solution spinning.

The fibers forming the fibrous non-woven web 29 may be made from a variety of materials including natural fibers, synthetic fibers, and combinations thereof. The choice of fibers may depend upon, for example, the intended end use of the finished web, the fiber cost and other factors. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or cross-linked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous non-woven substrate 23 may be formed from a single web 29 layer or multiple web layers. In the case of multiple layers, the layers are generally positioned in a juxtaposed or surface-to-surface relationship and all or a portion of the layers may be bound to adjacent layers. Thus, in one embodiment where the substrate 23 is formed of multiple web layers the second surface 27 of the non-woven substrate may be of the same material and construction as the skin-contact surface 25, or it may be of a different material and/or construction. It is also contemplated that the second surface 27 need not be defined by a non-woven web 29 to remain within the scope of this invention. For example, the non-woven substrate 23 may comprise a non-woven web 29 that is laminated or otherwise secured to a film or woven web (not shown) so that the second surface is defined by the film or woven web and is thus other than a fibrous non-woven web.

Airlaid non-woven webs are particularly well suited for personal care articles such as wet wipes 21. The basis weights for airlaid non-woven webs may suitably range from about 20 to about 200 grams per square meter (gsm) with staple fibers having a denier of about 0.5-10 and a length of about 6-15 millimeters. Wet wipes 21 may generally have a fiber density of about 0.025 g/cc to about 0.2 g/cc. Wet wipes may generally have a basis weight of about 20 gsm to about 150 gsm. More suitably the basis weight may be from about 30 to about 90 gsm. Even more suitably the basis weight may be from about 50 gsm to about 75 gsm. Processes for producing airlaid non-woven basesheets are described in, for example, published U.S. Pat. App. No. 2006/0008621, herein incorporated by reference.

Figure 2:
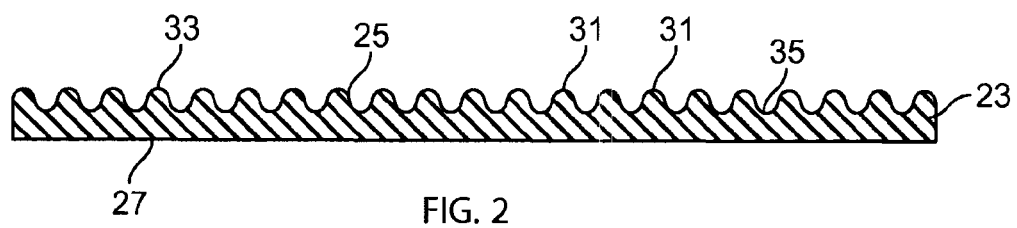
FIG. 2 is a cross-section taken in the plane of line 2-2 of FIG. 1.

The average thickness of the wipe 21 illustrated in FIGS. 1-2 is suitably in the range of at least about 0.25 mm to about 1.5 mm. More suitably, the average thickness of the wipe 21 may be between 0.3 mm and 1.0 mm. Even more suitably, the average thickness of the wipe may be between 0.5 mm and 1.0 mm. It is understood, however, that the wipe 21 may be of a lesser or greater thickness as set forth above without departing from the scope of this invention. It is also understood that for personal care articles other than wipes 21, the thickness of the non-woven substrate 23 may be in accordance with the intended function and use of the particular personal care article.

As illustrated in FIG. 2, at least the skin-contact surface 25 of the non-woven substrate 23 is configured to have a wave-form topography that matches a desired harmonic response of the human skin. As used herein, such a harmonic response is described in terms of one known model of mechanoreception referred to as a four-channel model and described particularly by G. A Gescheider et. al in *The Effects of Aging on Information-Processing Channels in the Sense of Touch: I. Absolute Sensitivity*, Sensory and Motor Research, Vol. 11, No. 4, 1994, pp. 345-347; and by Bolanowski et al. in *Four Channels Mediate the Mechanical Aspects of Touch*, The Journal of the Acoustical Society of America, Vol. 84(5), 1988, pp. 1680-1694. In this model, four information-processing channels exist for the human skin, with each channel being mediated by a morphologically distinct receptor type innervated by a specific nerve fiber type and tuned to a different range of frequencies. In general, the four psychophysical channels at their absolute thresholds have overlapping frequency characteristics for detection of sinusoidal vibration, with each channel optimally tuned to a specific region of the spectrum.

Figure 4:
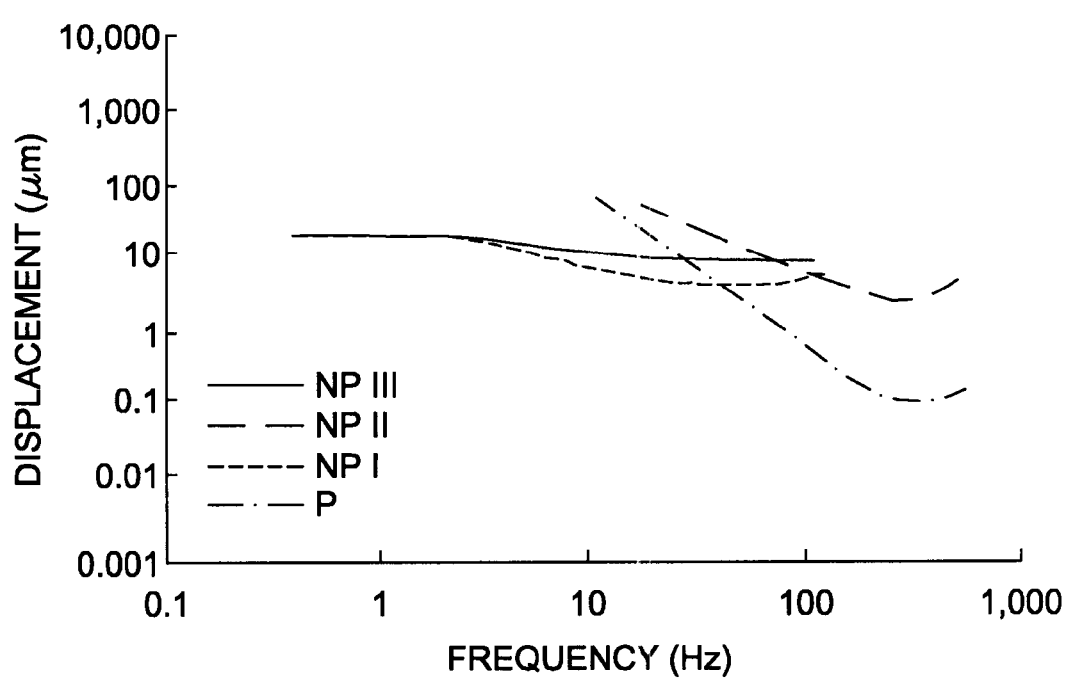
FIG. 4 is a graph of the relationship between sharpness frequency and displacement for multiple sensory channels.

Specifically, with reference to the data of FIG. 4 which is adopted from the Gescheider et. al. article (with the data revised to convert from decibel level to displacement), a P channel, mediated by Pacinean corpuscles (PC) and PC fibers, has a highly tuned U-shaped frequency characteristic with optimal sensitivity between 200-300 Hz and produces a sensation of vibration. A NP I channel, mediated by Meissner corpuscles and readily adapting (RA) fibers, is broadly tuned and produces sensations of flutter in the frequency range of 2-40 Hz. A NP II channel, mediated by Ruffini end organs and slowly adapting type II (SA II) fibers, is tuned at 200-400 Hz and responds over a wide range of frequencies. And a NP III channel, mediated by Merkel cell-neurite complexes and slowly adapting type I (SA I) fibers, produces a sensation of pressure in the frequency range of 0.4-2 Hz.

For a user to experience a tactile sensation a particular area or region of the skin must experience a combination of depth compression (e.g., from a surface or object pushing in against the skin to a certain depth) and frequency at which the area of the skin experiences the depth compression, such that the response thereto falls on or above one of the threshold lines for at least one of the channels in the above data plot. Consequently, when a response falls below all of the threshold lines, a tactile sensation is unlikely to be felt when the personal care article is in contact with a person's skin.

With respect to the frequency, when both the skin-contact surface 25 and the skin being treated remain stationary relative to each other upon contact (e.g., so that the contact is substantially limited to compressive contact), the frequency refers to a spatial frequency, which is defined by the density of or spacing between peaks of adjacent surface features disposed on the skin-contact surface of the substrate. Where the surface is moved (e.g., rubbed or wiped) over the skin in contact therewith, such as when applying a lotion or other treatment from a wet wipe to the skin or wiping a dry wipe over the skin, the rate at which the targeted area of the skin is contacted by the surface features (i.e., the frequency) is what is referred to herein as a temporal frequency and is a function of both the surface topography of the skin-contact surface 25 (e.g., the spatial frequency) and the speed at which the substrate 23 is moved over the area of the skin with the skin-contact surface of the substrate in contact with the skin.

As one example, consumer wipe usage patterns at different skin regions of the human body typically result in a range of movement speeds, or wipe speeds in the illustrated embodiment where the article is a wipe 21 (i.e., the rate at which the wipe is moved over the skin such as by rubbing or wiping in contact therewith), of about 2 to about 8 centimeters/second (cm/sec). Exemplary average wiping speeds for various skin regions and wipe users is provided in the following table.

| Skin Region | Adult Wiping Themselves | Caregiver Wiping Infant | Caregiver Wiping Adult |
|---|---|---|---|
| Vaginal | 2.5 | N/A | 2.5 |
| Face | 3.5 | 2.5 | 3.5 |
| Body | 5 | 3.5 | 6 |
| Buttock | 6 | 6 | 5 |
| Hand | 7.5 | 7.5 | 7.5 |

It is understood, however, that the substrate 23 movement speed relative to the skin may be slower or faster than the above range of speeds without departing from the scope of this invention.

In the embodiment illustrated in FIGS. 1 and 2, the skin-contact surface 25 of the wipe 21 (and more particularly of the substrate 23) comprises a plurality of surface features 31 defining a plurality of peaks 33 and corresponding valleys 35 that are sized and located so that the skin-contact surface has a generally topographical wave-form surface. More suitably, as illustrated in FIG. 2, the surface features 31 are sized and located in accordance with a sinusoidal wave-form in which the peaks 33 of the surface features are of uniform height above the respective valleys 35, and are uniformly spaced from each other, and are generally arcuate, or rounded, so that no corners are sharp edges are present at the peaks of the surface features. The surface features 31 are generally of a microstructure nature, e.g., on the order of about 0.001 to about 1,000 microns in height, and are more suitably in the range of about 0.1 to about 100 microns in height. Thus, it will be understood that the substrate 23 illustrated in FIGS. 1-3, and in particular the skin-contact surface 25 having the various surface features 31, is disproportionately sized for illustrative purposes (i.e., so that the surface features are more readily visible) and is not intended to be indicative of the actual size of the surface features or the size of the surface features relative to the dimensions of the substrate.

The surface features 31 of the illustrated wipe 21 are suitably formed integrally with (broadly, located on) the substrate 23. Such surface features 31 may be formed on the skin-contact surface 25 of the non-woven substrate 23, for example, by any of a variety of known non-woven web texturing techniques including, without limitation, molding, air-forming, bonding, embossing or other suitably technique. These surface features 31 may be formed by layering or concentrating material outward of the otherwise planar skin-contact surface 25, or the skin-contact surface of a planar substrate 23 may be compressed or densified in accordance with a sinusoidal pattern so as to form the valleys 35 into the surface 25 of the substrate, thereby defining the peaks 33 of the surface features. It also is contemplated that in other embodiments the surface features 31 may be formed separate from the substrate 23 and secured to (such as by adhesive, thermal or pressure bonding or other suitable securement technique) (broadly, located on) the substrate 23 to form the desired sinusoidal wave-form on the skin-contact surface 25 of the substrate. For example, the surface features 31 may comprise beads, polymers, inorganic/organic clays or other suitable materials or combinations thereof without departing from the scope of this invention.

In other embodiments the surface features 31 may be sprayed on, such as in the form of an ink or other suitable substance that adheres to the skin-contact surface of the substrate and extends outward therefrom to define the surface features. For example, in one such embodiment the substance may be printed on the substrate 23 by a suitable ink jet or wax jet printing apparatus to form the surface features 31.

Also in the illustrated embodiment of FIG. 1, the sinusoidal wave-form defined by the arrangement of surface features 31 is suitably the same in both the longitudinal and transverse (i.e., planar) directions of the substrate 23. It is contemplated, however, that the sinusoidal wave-form along the transverse direction, and in particular the period, or spatial frequency, may be different from that along the longitudinal direction so that the response provided by the wipe 21 may be different depending on the orientation (e.g., longitudinal or transverse) of the wipe as it is moved over the skin and/or it may depend on the direction in which the wipe is moved over the skin.

Figure 3:
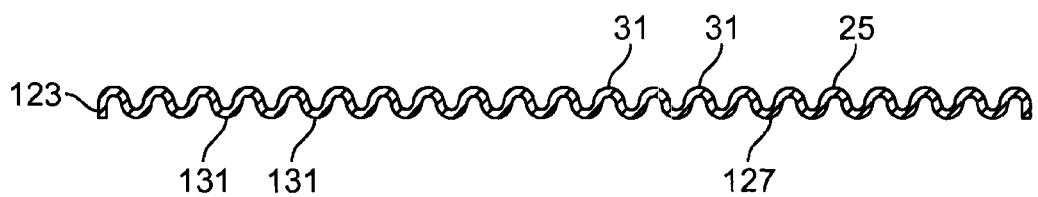
FIG. 3 is a cross-section similar to FIG. 2 but of a second embodiment of a personal care article.

Additionally, in the embodiment of FIGS. 1 and 2, the opposite or second surface 27 of the non-woven substrate is generally non-textured (i.e., it has no intended surface topography or is otherwise generally smooth). Alternatively, as illustrated in FIG. 3, the opposite surface 127 of the substrate 123 (particularly where the personal care article is a wipe as in the illustrated embodiment) may also comprise surface features 131, such as in a wave form identical to that defined by the surface features 31 on the skin-contact surface 25, or by a different pattern intended to result in a response that is different from the response achieved by the wave form of the surface features on the skin-contact surface. In such an embodiment, the skin-contact surface 25 is broadly referred to herein as a first skin-contact surface and the opposite surface is broadly referred to herein as a second skin-contact surface 127 of the substrate.

In accordance with one suitable embodiment, the surface features 31 of the substrate 23 are sized (e.g., in height, or amplitude) and located on the substrate (e.g., to define a spatial frequency) to be relatively highly sensitive without the surface features themselves being intended to aggressively treat (e.g., abrade, or exfoliate) the skin over which the wipe 21 is moved. In other embodiments the amplitude may be sufficient to aggressively, or mildly treat (e.g., abrade or exfoliate) the skin without causing noticeable discomfort to the user. More suitably, the surface features 31 are arranged in a sinusoidal wave-form having a relatively higher temporal frequency and relatively lower surface feature height, or amplitude.

For example, in one particularly suitable embodiment the sinusoidal wave-form has an amplitude (i.e., the height of each surface feature 31 from its base, or valley 35, to its peak 33) in the range of about 0.1 microns to about 10 microns, more suitably in the range of about 0.1 microns to about 5 microns, even more suitably in the range of about 0.1 microns to about 1 micron and still more suitably in the range of about 0.1 microns to about 0.5 microns. It is understood, however, that the amplitude may be other than within the above ranges without departing from the scope of this invention.

Even more suitably, the surface features 31 are located on the substrate 23 (e.g., spaced) relative to each other at least in part as a function of the movement speed (e.g., the wipe speed) at which the wipe 21 (and more particularly the skin-contact surface 25 of the substrate 23) is to be rubbed over one's skin so that the temporal frequency (i.e., the rate at which the surface features 31 come into contact with a targeted area of the skin as the substrate 23 is rubbed over that area) is in the range of about 100 Hz to about 1000 Hz. That is, the spatial frequency, or spacing between surface features 31, is such that upon movement of the substrate 23 over the skin at a selected or target movement speed, and more suitably within a range of possible movement speeds, the resultant temporal frequency is within the range of about 100 Hz to about 1000 Hz. More suitably the temporal frequency is within the range of about 100 Hz to about 500 Hz, still more suitably in the range of about 200 Hz to about 400 Hz, and even more suitably in the range of about 200 Hz to about 300 Hz. Still more suitably, the temporal frequency is about 250 Hz which as illustrated in the above data plot is generally the frequency at which the skin is most sensitive, particularly to the P-channel receptors.

Providing the skin-contact surface 25 with surface features 31 that define a sinusoidal wave-form topography having a relatively higher temporal frequency (e.g., in the range of about 100 Hz to about 1000 Hz) upon movement of the substrate 23 at the selected or target movement speed (e.g., the wipe 21 speed in the illustrated embodiment) over the skin allows the amplitude of the surface features to be relatively low (e.g., in the range of about 0.1 to about 10 microns) and still achieve the threshold level needed to provide a positive stimulatory event (i.e., so that the subject person can feel the surface features). For example, in using a wet wipe 21 to apply a lotion or other substance to the skin, the additional positive stimulatory event provides the person with a sensation that the lotion is working and providing a benefit to the skin, and may also provide a pleasing feel to the person.

In one particularly suitable embodiment, the amplitude of the surface features 31 and the spatial frequency thereof (i.e., the spacing between surface features) is such that the response is slightly above the response threshold throughout the entirety of a selected or target range of movement speeds (e.g., wipe speeds). As an example, in one embodiment of a method of making a substrate 23 comprising a skin-contact surface 25 having a plurality of surface features 31 arranged in a sinusoidal wave-form topography thereon, a suitable movement speed such as a specific movement speed (e.g., wipe speed), a range of movement speeds (e.g., in cm/sec), or average movement speed from a range of movement speeds is selected as a target, e.g., an expected average or typical movement speed used by consumers when wiping a particular skin region. A suitable temporal frequency or range of temporal frequencies (e.g., in Hz, which is cycles per second) is also selected.

A suitable surface feature 31 amplitude is determined (e.g., with reference to the above data plot) based on the four channel model described previously and more suitably at least in part as a function of the desired response and the selected temporal frequency. Thus, where the desired response is a positive sensory event, the surface feature 31 amplitude is selected such that the response throughout the selected temporal frequency range is at least at and is more suitably slightly above the threshold response level within the selected temporal frequency.

The spatial frequency, or spacing between surface features 31, is then determined as a function of the selected temporal frequency, or range of temporal frequency, and the selected movement speed, or range of movement speed of the substrate. In particular, the spacing between surface features 31 is determined as the selected movement speed (e.g., wipe 21 speed in the illustrated embodiment) divided by the selected temporal frequency. The following table provides more particular examples based on the wipe speeds provided in the previous table. In this table, the spatial distance (cm) between surface features 31 is determined for achieving a temporal frequency of about 250 Hz at the various wipe speeds selected previously.

| Skin Region | Adult Wiping Themselves | Caregiver Wiping Infant | Caregiver Wiping Adult |
|---|---|---|---|
| Vaginal | 0.01 | N/A | 0.01 |
| Face | 0.014 | 0.01 | 0.014 |
| Body | 0.02 | 0.014 | 0.024 |
| Buttock | 0.024 | 0.024 | 0.02 |
| Hand | 0.03 | 0.03 | 0.03 |

Thus, to achieve a temporal frequency of about 250 Hz, or 250 cycles per second, at a wipe speed of 2.5 cm/sec, the spatial distance between surface features 31 should be 2.5/250, or about 0.01 cm.

The spatial frequency and amplitude of the surface features of the skin-contact surface 25 of a substrate may be suitably determined via optics, profilometry, or other imaging techniques. One particularly suitable embodiment utilizes non-contact laser profilometry in which the surface is scanned in the X-Y-Z directions at various resolutions/spacing. The scanning should be such that a sufficient number of amplitude/wavelength ranges are scanned for measurements. The scanned data may be represented as point-cloud ASCII format or any other suitable format. Additionally, the data can be transformed as necessary from the range of point-cloud raw data to completed surface data that can be exported to a CAD system or any other suitable high-end surface format.

The amplitude and frequency (e.g., wavelength) determinations may be performed via various suitable analysis techniques and/or programs. For example, in one embodiment commercially available software such as that available from Geomagic of North Carolina, USA under the tradenames Geomagic Studio and Geomagic Qualify may be used. Within the analysis programs, measurements of amplitude and wavelength may be performed by "virtual" calipers or other measurement tools. In another suitable embodiment the profilometry data may be displayed as color coded elevation maps to highlight surface relief and repeating patterns. Closely spaced (e.g., high frequency) pattern repetition is then analyzed by the extracting the "power" spectrum, which shows a distribution of common wavelengths, up to about 7 mm, within the dimensions of the area sampled.

It is also contemplated that a line or series of personal care articles (e.g., at least a first personal care article and a second personal care article) each having a substrate 23 comprising a skin-contact surface 25 having a plurality of surface features 31 arranged in a sinusoidal wave-form topography thereon may be made with each article in the line of articles configured for use in wiping a different region of the body such as the vaginal region, facial region, body region, buttock region or hand region. In particular, the spacing between surface features 31 on the contact surface 25 of each article is different from the surface feature spacing of each other article in the series, with the spacing of surface features of each article being at least in part a function of the movement speed that corresponds with the particular skin region on which the article is to be used.

In another embodiment, the skin-contact surface 25 may be configured as a more aggressive surface such that it may be used, for example, to exfoliate the skin while minimizing the perception of abrasion (i.e., without the person whose skin is being treated having a negative or uncomfortable feeling). In such an embodiment, the surface features 31 are suitably sized (e.g., in height, or amplitude) and located on the substrate 23 (e.g., in spatial frequency, or spacing between surface features) to be substantially less sensitive to the person while the surface features themselves aggressively treat (e.g., abrade, or exfoliate) the skin over which the substrate is moved. More suitably, the surface features 31 are located on the skin-contact surface 25 of the substrate 23 in a sinusoidal wave-form such that at the selected substrate movement speed (e.g., wipe speed in the illustrated embodiment) or range of movement speeds the temporal frequency is relatively low, where the human skin is less sensitive (e.g., where the NP-III channel receptor defines the response threshold), and such that the surface feature height, or amplitude is relatively higher for a more aggressive skin treatment.

For example, in one particularly suitable embodiment the sinusoidal wave-form defined by the surface features 31 has an amplitude (i.e., the height of each surface feature from its base, or valley 35, to its peak 33) in the range of about 0.1 microns to about 30 microns, more suitably about 1 micron to about 10 microns, and even more suitably about 1 micron to about 5 microns.

Even more suitably, the surface features 31 are located (e.g., spaced) relative to each other on the substrate 23 at least in part as a function of the substrate movement speed (e.g., the wipe 21 speed in the illustrated embodiment) at which the substrate is to be rubbed over the skin to be treated so that the temporal frequency (i.e., the rate at which the surface features come into contact with a targeted area of the skin as the substrate is rubbed over that area) is in the range of about 1 Hz to about 10 Hz, and more suitably in the range of about 1 Hz to about 5 Hz. That is, the spatial frequency, or spacing between surface features 31, is such that upon movement of the substrate over the skin at a selected movement speed, and more suitably within a range of movement speeds, the resultant temporal frequency is within the range of about 1 Hz To about 10 Hz and more suitably about 1 Hz to about 5 Hz.

At such a lower temporal frequency the surface features 31 may have a higher amplitude (e.g., in the range of about 0.1 to about 30 microns or otherwise as set forth above) for more aggressively treating the skin. However, because the frequency is in a less sensitive, lower range the larger surface features 31 will still not evoke a stimulatory response, or will be lightly perceptible. That is, while the surface features 31 are relatively higher and therefore provide a coarser surface, the response caused by these surface features at the lower temporal frequency is still below, on or only slightly above the response threshold at which the user would experience a sensory event. As a result, the substrate 23 (and hence the personal care article or wipe 21) may be used to aggressively treat a person's skin without the person feeling the discomfort of rubbing the rough surface against the skin.

In one particularly suitable embodiment, the amplitude of the surface features 31 and the spatial frequency thereof (i.e., the spacing between peaks 33 of the surface features) is such that the response is slightly below the response threshold level throughout the entirety of a selected range of substrate movement speeds. As an example, in another embodiment of a method of making a substrate 23 comprising a skin-contact surface 25 having a plurality of surface features 31 arranged in a sinusoidal wave-form thereon, a suitable movement speed (e.g., wipe speed) or range of movement speeds (e.g., in cm/sec) is selected as a target, such as an expected average or typical movement speed used by consumers when wiping a particular skin region. A suitable temporal frequency or range of temporal frequencies (e.g., in Hz, which is cycles per second) is selected. A suitable surface feature 31 amplitude is also selected (e.g., with reference to the above data plot)

based on the four channel model described previously and at least in part as a function of the selected temporal frequency and the desired response. Thus, where the desired response is to reduce or eliminate the sensory perception by the skin owner, the surface feature 31 amplitude is selected such that the response within the selected temporal frequency range is suitably below the threshold response level for that frequency range. If a positive sensory event is desired, the amplitude is selected such that within the selected temporal frequency range the response is above the threshold response level.

The spatial frequency, or spacing between surface features 31, is then determined as a function of the selected temporal frequency and the selected movement speed, or speeds of the substrate 23 relative the skin. In particular, the spacing between surface features 31 is determined as the selected movement speed divided by the selected temporal frequency. The following table provides more particular examples based on the wipe speeds provided in the previous table. In this table, the spatial distance (cm) between surface feature peaks 33 is determined for achieving a temporal frequency of about 1 Hz at the various wipe speeds selected previously.

| Skin Region | Adult Wiping Themselves | Caregiver Wiping Infant | Caregiver Wiping Adult |
| --- | --- | --- | --- |
| Vaginal | 2.5 | N/A | 2.5 |
| Face | 3.5 | 2.5 | 3.5 |
| Body | 5 | 3.5 | 6 |
| Buttock | 6 | 6 | 5 |
| Hand | 7.5 | 7.5 | 7.5 |

It also contemplated that in other embodiments the amplitude (e.g., height) of the surface features 31 may be selected to aggressively treat one's skin while also providing a positive sensory event and remain with the scope of this invention.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description shall be interpreted as illustrative and not in a limiting sense.

What is claimed is:

1. A personal care article for contact with human skin upon movement of the article over the skin at a movement speed of the article relative to the skin, said article comprising:
    a non-woven substrate having a longitudinal direction, a transverse direction and at least one skin-contact surface;
    a plurality of surface features disposed on the at least one skin-contact surface in a sinusoidal wave-form along at least one of the longitudinal direction and the transverse direction of the substrate, the surface features having a uniform height that generally defines an amplitude of the sinusoidal wave-form, said height being in the range of about 0.1 microns to about 30 microns, said surface features being spaced from each other a spatial distance, said spatial distance being at least in part a function of the movement speed at which the article is to be moved relative to the skin while in contact therewith.

2. The personal care article set forth in claim 1 wherein the surface features are disposed on the skin-contact surface in a sinusoidal wave-form along both the longitudinal and the transverse directions of the substrate.

3. The personal care article set forth in claim 2 wherein the spatial distance between the surface features is generally uniform in both the longitudinal and the transverse directions of the substrate.

4. The personal care article set forth in claim 1 wherein the uniform height of the surface features is in the range of about 0.1 microns to about 10 microns.

5. The personal care article set forth in claim 1 wherein the spatial distance between the surface features is uniform and in the range of about 0.01 to about 0.03 centimeters.

6. The personal care article set forth in claim 1 wherein the spatial distance between the surface features is uniform and in the range of about 2.5 to about 7.5 centimeters.

7. The personal care article set forth in claim 1 wherein the substrate has a first skin-contact surface and a second skin-contact surface opposite the first skin-contact surface, each of the first and second skin-contact surfaces having a plurality of surface features disposed thereon in a sinusoidal wave-form along at least one of the longitudinal direction and the transverse direction of the substrate, the surface features of each of said first and second skin-contact surfaces having a height that generally defines an amplitude of the sinusoidal wave-form, said surface features being spaced from each other a spatial distance, said spatial distance being at least in part a function of the movement speed at which the article is to be moved relative to the skin while in contact therewith.

8. The personal care article set forth in claim 7 wherein the surface features of the first skin-contact surface are spaced from each other a first distance and the surface features of the second skin-contact surface are spaced from each other a second distance substantially equal to the first distance.

9. A personal care article for contact with human skin upon movement of the article over the skin at a movement speed of the article relative to the skin, said article comprising:
    a non-woven substrate having a longitudinal direction, a transverse direction and at least one skin-contact surface;
    a plurality of surface features disposed on the at least one skin-contact surface in a sinusoidal wave-form along at least one of the longitudinal direction and the transverse direction of the substrate, the surface features being sized and located on the skin-contact surface of the non-woven substrate to evoke, upon movement of the article over the skin in contact therewith, a positive stimulatory response of a P-channel skin receptor of a four-channel model of mechano-reception in the range of about 100 Hz to about 1000 Hz, wherein the surface features have a uniform height in the range of about 0.1 microns to about 30 microns.

10. The personal care article set forth in claim 9 wherein the surface features have a uniform height in the range of about 0.1 microns to about 10 microns.

11. A series of personal care articles for contact with the human skin, said series of articles comprising:
    a first personal care article for contact with human skin upon movement of the article over the skin at a first movement speed of the article relative to the skin, said first personal care article comprising a first non-woven substrate having a longitudinal direction, a transverse direction and at least one skin-contact surface, and a plurality of surface features disposed on the at least one skin-contact surface in a sinusoidal wave-form along at least one of the longitudinal direction and the transverse direction of the first substrate, the surface features having a uniform height that generally defines an amplitude of the sinusoidal wave-form, said surface features being spaced from each other a first spatial distance, said first spatial distance being at least in part a function of the first movement speed at which the first article is to be moved relative to the skin while in contact therewith, wherein the height of the surface features is in the range of about 0.1 microns to about 30 microns; and a second personal care article for contact with human skin upon movement of the article over the skin at a second movement speed of the article different from the first movement speed at which the first personal care article is moved relative to the skin, said second personal care article comprising a second non-woven substrate having a longitudinal direction, a transverse direction and at least one skin-contact surface, and a plurality of surface features disposed on the at least one skin-contact surface in a sinusoidal wave-form along at least one of the longitudinal direction and the transverse direction of the second substrate, the surface features having a uniform height that generally defines an amplitude of the sinusoidal wave-form, said surface features being spaced from each other a second spatial distance different from the first spatial distance, said second spatial distance being at least in part a function of the second movement speed at which the second article is to be moved relative to the skin while in contact therewith, wherein the height of the surface features is in the range of about 0.1 microns to about 30 microns.

* * * * *